(12) United States Patent
Bastings et al.

(10) Patent No.: US 8,575,402 B2
(45) Date of Patent: Nov. 5, 2013

(54) PROCESS FOR THE PRODUCTION OF ALKYLENE GLYCOL

(75) Inventors: Roel Guillaume Hubertus Leonardus Bastings, Amsterdam (NL); Arthur Willibrordus Titus Rots, Amsterdam (NL)

(73) Assignee: Shell Oil Company, Houston, TX (US)

( * ) Notice: Subject to any disclaimer, the term of this patent is extended or adjusted under 35 U.S.C. 154(b) by 245 days.

(21) Appl. No.: 13/274,536

(22) Filed: Oct. 17, 2011

(65) Prior Publication Data
US 2012/0095271 A1 Apr. 19, 2012

(30) Foreign Application Priority Data
Oct. 19, 2010 (EP) .................................... 10188066

(51) Int. Cl.
*C07C 27/02* (2006.01)
(52) U.S. Cl.
USPC ............................ 568/858; 568/852; 568/857
(58) Field of Classification Search
None
See application file for complete search history.

(56) References Cited

U.S. PATENT DOCUMENTS 7,145,045 B2 * 12/2006 Harmsen et al. .............. 568/867

FOREIGN PATENT DOCUMENTS

WO WO2004089866 10/2004 ............. C07C 68/06

* cited by examiner

*Primary Examiner* — Sudhakar Katakam

(57) ABSTRACT

The invention provides a process for the production of an alkylene glycol comprising converting an alkene to the corresponding alkylene oxide; absorbing the alkylene oxide in an aqueous absorbent and then stripping; supplying the aqueous alkyene oxide stream to a carboxylation reactor; converting the alkylene oxide to a corresponding alkylene carbonate; converting the alkylene carbonate to the alkylene glycol; removing water to form a dehydrated alkylene glycol stream; and purifying the dehydrated alkylene glycol stream, wherein the start-up procedure comprises supplying water, carboxylation-hydrolysis catalyst and carbon dioxide streams to the carboxylation reactor and providing a start-up stream comprising the alkylene glycol at an injection point at or downstream of the inlet used in supplying the stream to the carboxylation reactor and recovering an alkylene glycol stream from the glycol distillation column.

8 Claims, 4 Drawing Sheets

PROCESS FOR THE PRODUCTION OF ALKYLENE GLYCOL

This application claims the benefit of European Application 10188066.4 filed Oct. 19, 2010.

FIELD OF THE INVENTION

The present invention relates to process for the production of an alkylene glycol from an alkene, comprising a specific start-up procedure.

BACKGROUND OF THE INVENTION

Monoethylene glycol is used as a raw material in the manufacture of polyester fibres, polyethylene terephthalate (PET) plastics and resins. It is also incorporated into automobile antifreeze liquids.

Monoethylene glycol is typically prepared from ethylene oxide, which is in turn prepared from ethylene. In order to produce ethylene oxide, ethylene and oxygen are passed over a silver oxide catalyst, typically at pressures of 10-30 bar and temperatures of 200-300° C., producing a product stream comprising ethylene oxide, carbon dioxide, ethylene, oxygen and water. The amount of ethylene oxide in the product stream is usually between about 0.5 and 10 weight percent. The product stream is supplied to an ethylene oxide absorber and the ethylene oxide is absorbed by a recirculating solvent (absorbent) stream containing mostly water. After absorption, the aqueous ethylene oxide stream is sent to a stripper in order to separate the ethylene oxide. The ethylene oxide leaves the top of the stripper as a concentrated aqueous ethylene oxide stream.

In one well-known process, ethylene oxide is then catalytically reacted with carbon dioxide to produce ethylene carbonate. The ethylene carbonate is subsequently hydrolysed to provide ethylene glycol. Reaction via ethylene carbonate significantly improves the selectivity of ethylene oxide conversion to monoethylene glycol compared to the known process wherein ethylene oxide is reacted with a large excess of water to form ethylene glycol in a non-catalytic process.

Such a process for the production of ethylene glycol via ethylene carbonate can be run in series with the process for the production of ethylene oxide. That is, the ethylene oxide is not purified after absorption and stripping, but is supplied to a carboxylation reactor as the concentrated aqueous stream from the top of the stripper.

During the start-up of such a combined process, the ethylene oxide to ethylene glycol section of the plant is prepared to receive an aqueous ethylene oxide stream before such a stream is actually provided. To this end, this section of the plant is heated up, pressurized and several internal recycles, such as catalyst, CO2 and internal liquid recycles are established. A water stream is supplied to the carboxylation reactor and is removed from the process, further downstream, via a dehydrator.

Problems may occur in the ethylene oxide to ethylene glycol part of the process at a stage where little or no aqueous ethylene oxide is being produced in the ethylene to ethylene oxide part of the process. At this stage, the feed streams being supplied to the process, and passing through the carboxylation and hydrolysis stages, will be a concentrated catalyst stream, a carbon dioxide stream and water. When only these feeds are passed through the process, instead of the desired concentrated solution of catalyst in a catalyst separation section and dilute solutions of catalysts in the rest of the ethylene oxide to ethylene glycol section of the plant, a homogenous distribution of the catalyst solution throughout the entire ethylene oxide to ethylene glycol section of the plant will result. Alternatively, certain sections of the plant (e.g. the catalyst separation section) must be bypassed until an aqueous ethylene oxide stream is being provided. These sections must then be started-up separately, at a later stage, adding to the complexity of the overall start-up process.

The present inventors have sought to provide an improved start-up procedure for this process for the production of an alkylene glycol from an alkene allowing avoidance of the above problems and an overall increase in efficiency of the process.

SUMMARY OF THE INVENTION

Accordingly, the present invention provides a process for the production of an alkylene glycol from an alkene comprising the steps of:

i) converting the alkene in the presence of oxygen and an epoxidation catalyst to the corresponding alkylene oxide in an epoxidation reactor;

ii) absorbing the alkylene oxide in an aqueous absorbent and then stripping said absorbent to provide an aqueous alkylene oxide stream;

iii) supplying the aqueous alkyene oxide stream at an inlet to a carboxylation reactor;

iv) converting the aqueous alkylene oxide stream in the presence of one or more carboxylation-hydrolysis catalysts and carbon dioxide to a stream comprising the corresponding alkylene carbonate in one or more carboxylation reactors;

v) converting the stream comprising the alkylene carbonate to a stream comprising the alkylene glycol in one or more hydrolysis reactors;

vi) removing water from the stream comprising the alkylene glycol to form a dehydrated alkylene glycol stream in one or more dehydration columns;

vii) purifying the dehydrated alkylene glycol stream in one or more glycol distillation columns to form a purified alkylene glycol product stream and a carboxylation-hydrolysis catalyst recycle stream, wherein the start-up procedure for said process comprises supplying water, carboxylation-hydrolysis catalyst and carbon dioxide streams to the carboxylation reactor and providing a start-up stream comprising the alkylene glycol at an injection point at or downstream of the inlet used in step iii) and recovering an alkylene glycol stream from the glycol distillation column.

DETAILED DESCRIPTION OF THE INVENTION

Figure 1:
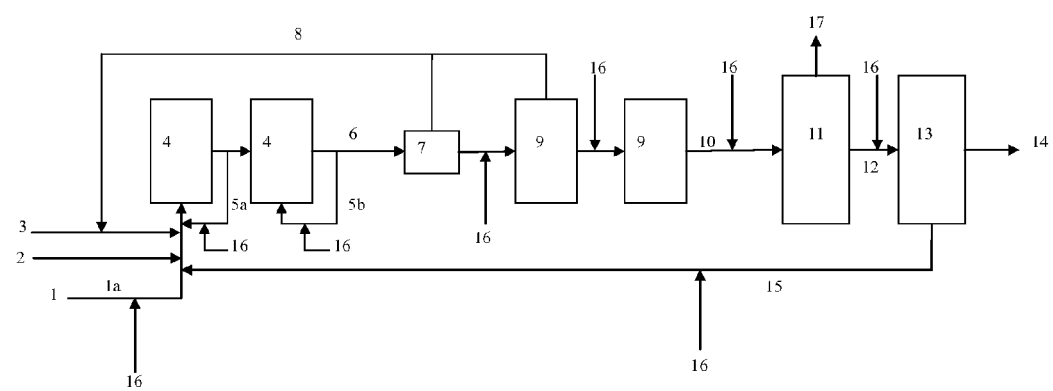
FIG. 1 is a schematic diagram showing a process according to an embodiment of the invention.

The present invention provides a process for the production of an alkylene glycol from an alkene, comprising a specific start-up procedure. Said process involves the reactions set out below:

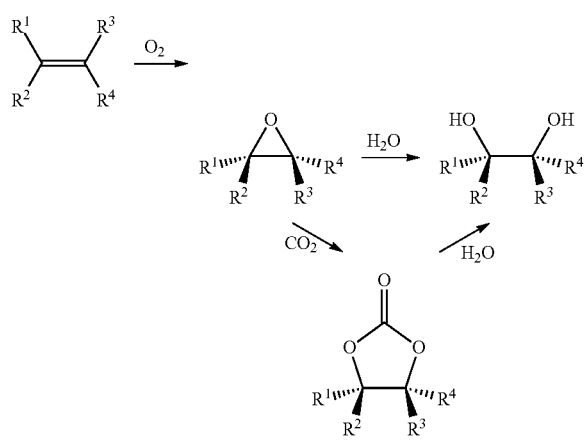

R1, R2, R3 and R4 are preferably chosen from hydrogen or an optionally substituted alkyl group having from 1 to 6 carbon atoms, more preferably from 1 to 3 carbon atoms. As substituents, moieties such as hydroxy groups may be present. Preferably, R1, R2 and R3 represent hydrogen atoms and R4 represents hydrogen or a non-substituted C1-C3-alkyl group and, more preferably, R1, R2, R3 and R4 all represent hydrogen atoms.

Examples of suitable alkenes therefore include ethylene and propylene. In the present invention, the most preferred alkene is ethylene.

Thus, the process of the present invention may be a process for the production of ethylene glycol or propylene glycol, via the epoxidation of ethylene or propene to ethylene oxide or propylene oxide, respectively.

The alkene is reacted with oxygen in the presence of a catalyst in a reactor to produce a gas composition comprising alkylene oxide, alkene, oxygen, carbon dioxide and water vapour. The oxygen may be supplied as oxygen or as air, but is preferably supplied as oxygen. Ballast gas, for example methane or nitrogen, is typically supplied to allow operation at high oxygen levels without causing a flammable mixture. Moderator, e.g. monochloroethane or dichloroethane, may be supplied for ethylene oxide catalyst performance control. The alkene, oxygen, ballast gas and moderator are preferably supplied to recycle gas that is supplied to the alkylene oxide reactor from the alkylene oxide absorber (optionally via a carbon dioxide absorption column).

The epoxidation reactor is typically a multitubular, fixed bed reactor. The catalyst is preferably finely dispersed silver and optionally promoter metals on a support material, for example, alumina. The reaction is preferably carried out at pressures of greater than 1 MPa and less than 3 MPa and temperatures of greater than 200® C. and less than 300® C. The gas composition from the epoxidation reactor is preferably cooled in one or more coolers, preferably with generation of steam at one or more temperature levels.

Contaminants are removed from the gas composition before it is supplied to the alkylene oxide absorber. Possible contaminants include acids, esters, aldehydes, acetals and organic halides. A preferred method of removing contaminants is quenching, preferably by contacting the gas composition with a cooled recirculating aqueous solution.

The gas composition from the epoxidation step is then supplied to an alkylene oxide absorber comprising a column of vertically stacked trays or comprising a packed column.

Lean absorbent is supplied to the alkylene oxide absorber and is contacted with the gas composition in the alkylene oxide absorber. Fat absorbent, comprising components absorbed from the gas composition including alkylene oxide, CO2 and light ends, is withdrawn from the alkylene oxide absorber.

The lean absorbent comprises at least 50 wt % water. Preferably, the lean absorbent comprises at least 80 wt % water.

The fat absorbent withdrawn from the absorber is supplied to a stripper. An aqueous alkylene oxide stream is produced from the top of the stripper. The remaining absorbent, now lean absorbent, is recycled to the alkylene oxide absorber.

The aqueous alkylene oxide stream from the top of the stripper suitably contains at least 50 wt % alkylene oxide, preferably at least 55 wt %. In certain embodiments, a stripper-concentrator is used, wherein the top product from the stripper is further concentrated. In these embodiments, the aqueous alkylene oxide stream may contain at least 95 wt % alkylene oxide. In these embodiments, the aqueous alkylene oxide stream is diluted with water before being provided to the alkylene oxide to alkylene glycol section of the process.

In the present invention, a carboxylation-hydrolysis catalyst is one which promotes carboxylation and/or hydrolysis.

The afore-mentioned aqueous alkylene oxide stream is provided to the alkylene oxide to alkylene glycol section of the process and is supplied to a carboxylation reactor via an inlet. Carbon dioxide and a carboxylation-hydrolysis catalyst stream are also provided. The carbon dioxide and carboxylation-hydrolysis catalyst streams may be provided to the carboxylation reactor separately from the aqueous alkylene oxide stream. Preferably, the carbon dioxide and carboxylation-hydrolysis catalyst streams are combined with the aqueous alkylene oxide stream prior to the aqueous alkylene oxide stream being supplied to the carboxylation reactor via an inlet.

The carboxylation-hydrolysis catalyst stream comprises one or more catalysts that promote carboxylation and hydrolysis. If only one carboxylation-hydrolysis catalyst is present, then the catalyst must promote carboxylation and hydrolysis. If two or more carboxylation-hydrolysis catalysts are present, then each carboxylation-hydrolysis catalyst can promote either carboxylation or hydrolysis or can promote both reactions (provided that at least one carboxylation-hydrolysis catalyst promotes carboxylation and at least one carboxylation-hydrolysis catalyst promotes hydrolysis).

In the present invention, the one or more carboxylation-hydrolysis catalysts that promote carboxylation and hydrolysis is/are homogeneous. Homogeneous carboxylation-hydrolysis catalysts that are known to promote carboxylation include alkali metal halides such as potassium iodide and potassium bromide, and halogenated organic phosphonium or ammonium salts such as tributylmethylphosphonium iodide, tetrabutylphosphonium iodide, triphenylmethylphosphonium iodide, triphenyl-propylphosphonium bromide, triphenylbenzylphosphonium chloride, tetraethylammonium bromide, tetramethylammonium bromide, benzyltriethylammonium bromide, tetrabutylammonium bromide and tributylmethylammonium iodide. Homogeneous carboxylation-hydrolysis catalysts that are known to promote hydrolysis include basic alkali metal salts such as potassium carbonate, potassium hydroxide and potassium bicarbonate, or alkali metal metalates such as potassium molybdate. Preferred homogeneous catalyst systems include a combination of potassium iodide and potassium carbonate, and a combination of tributylmethylphosphonium iodide and potassium carbonate.

The carboxylation-hydrolysis catalyst stream is supplied to the carboxylation reactor either separately or after mixing with the aqueous alkylene oxide and/or CO2 streams. After carboxylation, hydrolysis and dehydration, it is separated from the product stream in the catalyst separation section of the glycol distillation column. As the process of the present invention proceeds, a carboxylation-hydrolysis catalyst recycle stream from the catalyst separation section will be recycled to the carboxylation step.

Carboxylation of the aqueous alkylene oxide stream in the presence of carbon dioxide to produce a stream comprising the corresponding alkylene carbonate occurs in one or more carboxylation reactors. If more than one reactor is present, they are preferably arranged in series. As used herein, when the phrases 'supplied to the carboxylation reactor' and 'supplied to a carboxylation reactor' are used and more than one carboxylation reactor is present, the stream is being supplied to the first carboxylation reactor of the one or more in series.

The carboxylation reactors are suitably two-phase flow reactors operating at a pressure in the range of from 0.8 to 3.0 MPa and a temperature in the range of from 50 to 180° C.

The carboxylation reactors will preferably each be provided with a liquid recycle wherein liquid is removed from the reactor and then recycled to the bottom of the reactor. The recycle stream can be heated or cooled in order to provide improved temperature control to the carboxylation reactor.

After the aqueous alkylene oxide stream is converted to a stream comprising the corresponding alkylene carbonate in the one or more carboxylation reactors, the stream comprising the alkylene carbonate is then converted to a stream comprising the alkylene glycol in one or more hydrolysis reactors.

However, in a preferred embodiment of the process of the present invention, prior to being supplied to the one or more hydrolysis reactors, the stream comprising the alkylene carbonate is subjected to a carbon dioxide separation step in a CO2 separation vessel. In this step, carbon dioxide is removed from the stream comprising the alkylene carbonate and the carbon dioxide may then be recycled to the carbon dioxide stream to be supplied to the carboxylation reactor.

The one or more hydrolysis reactors may be any suitable reactor type. Preferably, the hydrolysis reactors are baffled reactors. If there is more than one hydrolysis reactor it is preferred that the hydrolysis reactors are connected in series.

In one embodiment of the invention, at least one of the one or more hydrolysis reactors is a baffled reactor, wherein the baffled reactor has at least 3, preferably at least 4 compartments, the compartments are formed by internal baffles and the internal baffles provide a sinuous route for reaction fluid through the reactor. Optionally, steam is injected into the baffled reactor.

Carbon dioxide may be produced in the one or more hydrolysis reactors and is preferably separated from the product stream as it leaves the one or more hydrolysis reactors and recycled to the carbon dioxide stream to be supplied to the carboxylation reactor.

The temperature in the one or more hydrolysis reactors is typically from 100 to 200® C., preferably from 100 to 180® C. The pressure in the one or more hydrolysis reactors is typically from 0.1 to 3 MPa.

The stream comprising alkylene glycol from step v) is supplied to a dehydrator. The stream that is supplied to the dehydrator preferably comprises very little alkylene oxide or alkylene carbonate, i.e. most of the alkylene oxide or alkylene carbonate has been converted to alkylene glycol prior to supply to the dehydrator column. Preferably, the molar ratio of alkylene glycol to alkylene oxide and alkylene carbonate (combined) in the stream supplied to the dehydrator is greater than 90:10, more preferably greater than 95:5, most preferably greater than 99:1. Water is recovered from the dehydrator and may be recycled or may be sent to wastewater.

The dehydrator is preferably one or more dehydration columns, including at least one vacuum column, preferably operating at a pressure of less than 0.05 MPa, more preferably less than 0.025 MPa and most preferably about 0.0125 MPa.

The dehydrated alkylene glycol stream from step vi) is then purified to remove impurities and provide a purified alkylene glycol product stream. The one or more homogeneous carboxylation-hydrolysis catalysts from the dehydrated product stream, are separated in the catalyst separation section to provide a carboxylation-hydrolysis catalyst recycle stream. The carboxylation-hydrolysis catalyst recycle stream is then supplied to the carboxylation reactor.

The start-up procedure of the present invention may be carried out at any point when there is little or no aqueous alkylene oxide stream being supplied to the carboxylation reactor. This may occur at initial start-up of the process or if the process has been tripped and needs to be re-started. Generally the start-up procedure will be started before supply of oxygen to the alkylene oxide reactor is started.

It should be understood that the start-up procedure may continue after an aqueous alkylene oxide stream is being supplied to the carboxylation reactor. Suitably, the amount of start-up stream comprising alkylene glycol will compensate for the expected volume of aqueous alkylene oxide stream at which the process is normally run. As the amount of aqueous alkylene oxide stream being provided increases over time, the amount of start-up stream comprising alkylene glycol can be reduced. Once the process is running at its normal start-up procedure will be stopped. In a preferred embodiment of the present invention, the amount of start-up stream comprising alkylene glycol provided will maintain the catalyst concentration at a steady level in the carboxylation reactors. This level is suitably at least 3 wt %, preferably at least 4 wt % based on the total weight of the reaction mixture. This level is suitably at most 10 wt %, preferably at most 8 wt %, more preferably at most 6 wt % based on the total weight of the reaction mixture.

In the start-up procedure of the present invention, the start-up stream comprising alkylene glycol is initially supplied from an external source. The start-up stream comprising the alkylene glycol is provided at an injection point in the process at or downstream of step iii).

Suitably, the start-up stream is provided at any one of the following injection points which are at or downstream of the inlet used in step iii): upstream of the one or more carboxylation reactors; in the liquid recycle stream recycled into any one of the one or more carboxylation reactors; between the carboxylation reactors and the one or more hydrolysis reactors; between the hydrolysis reactors if there is more than one hydrolysis reactor present; after the one or more hydrolysis reactors and before the dehydrator; into the dehydrated alkylene glycol stream before the glycol distillation column; or into the catalyst recycle stream.

Figure 2:
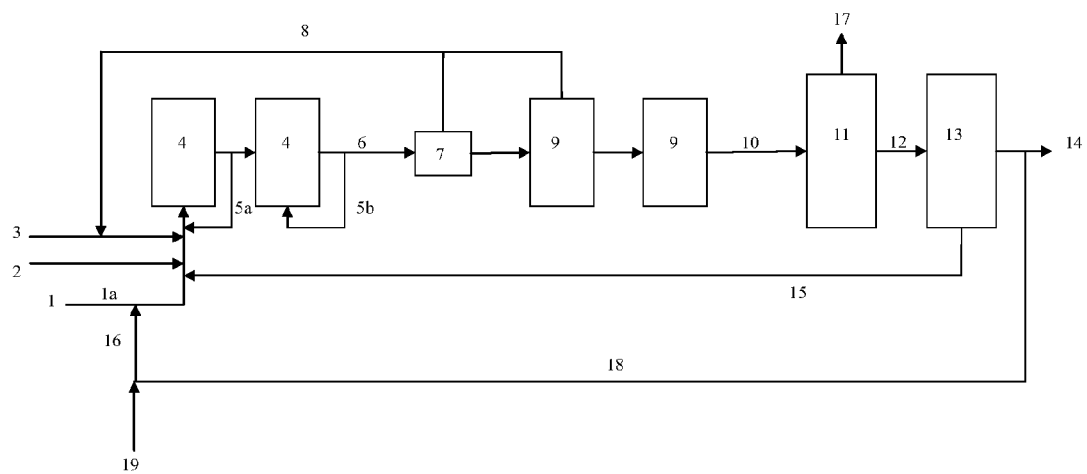
FIG. 2 is a schematic diagram showing a process according to one preferred embodiment of the invention.
Figure 3:
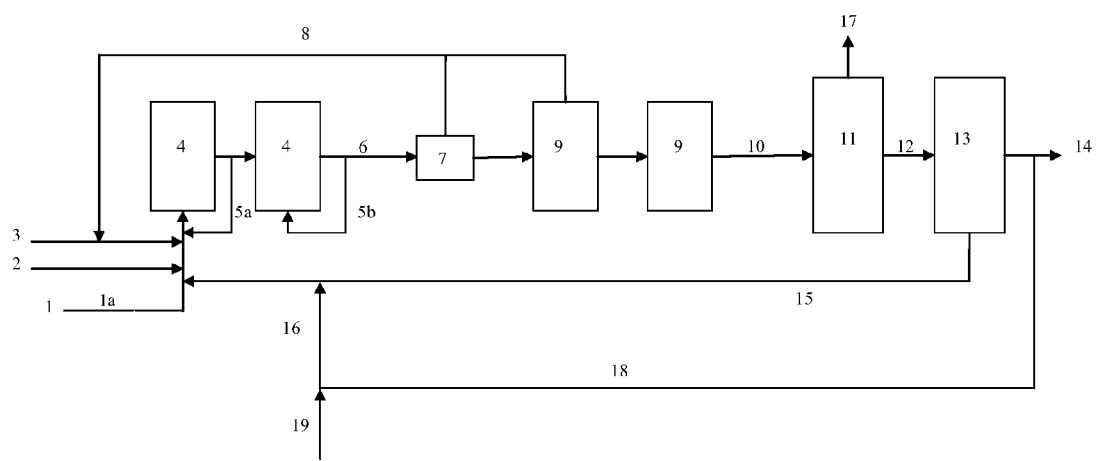
FIG. 3 is a schematic diagram showing a process according to another preferred embodiment of the invention.
Figure 4:
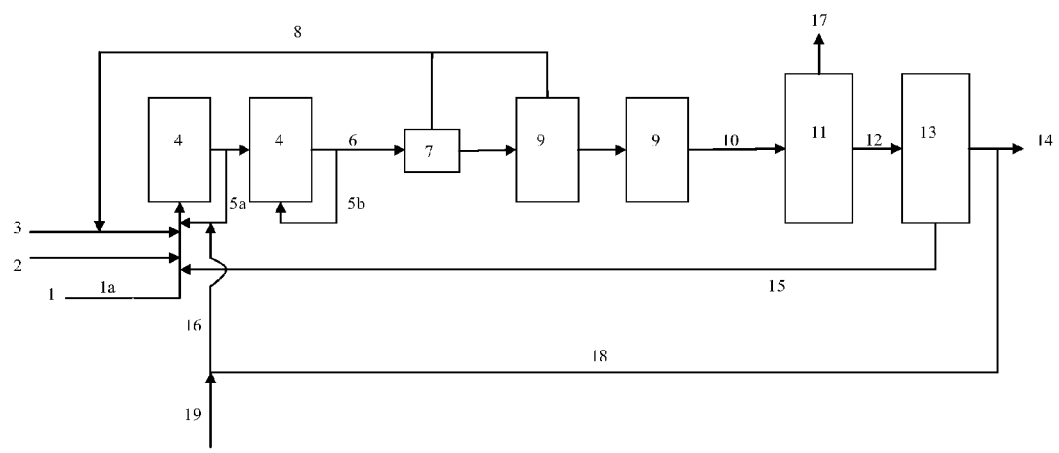
FIG. 4 is a schematic diagram showing a process according to a further preferred embodiment of the invention.

It will be appreciated that an injection point at the inlet used in step iii) may simultaneously be considered as being upstream of the carboxylation reactor; in the liquid recycle stream recycled into any one of the one or more carboxylation reactors; or into the catalyst recycle stream. FIGS. 2-4 herein display such embodiments of the present invention.

On the other hand, an injection point downstream of the inlet used in step iii) may simultaneously be considered as being downstream of the carboxylation reactor, for example, between the carboxylation reactors and the one or more hydrolysis reactors; between the hydrolysis reactors if there is more than one hydrolysis reactor present; after the one or more hydrolysis reactors and before the dehydrator; or into the dehydrated alkylene glycol stream before the glycol distillation column.

Preferably, the start-up stream is provided upstream of the one or more carboxylation reactors or into the catalyst recycle stream. In these preferred embodiments, the start-up procedure allows control of the water/alkylene glycol/catalyst ratio across the largest part of the alkylene oxide to alkylene glycol section of the process.

During the start-up procedure an alkylene glycol stream is recovered from the glycol distillation column. Initially, this stream will comprise the start-up stream. However, it should be understood that changes to its exact composition may have occurred during the procedure. As the start-up procedure proceeds and an aqueous alkylene oxide stream starts to be provided to the process, further alkylene glycol will be produced and this will also be recovered from the glycol distillation column as a purified alkylene glycol stream.

In one preferred embodiment of the present invention, the alkylene glycol stream is recovered from the glycol distillation column and is recycled to the injection point, optionally after intermediate storage. In this embodiment, as the start-up procedure continues, only a portion of the alkylene glycol stream from the glycol distillation column will need to be recycled to the injection point. The rest may be recovered as the desired product of the process of the present invention.

The water stream supplied to the carboxylation during the start-up procedure will be removed from the system in the glycol dehydrator and may be recycled or disposed of as wastewater.

The CO2 recycle stream must be established during the start-up of the process of the present invention. CO2 will be produced in the alkylene to alkylene oxide section of the plant when it is active, but at start-up, insufficient CO2 will be supplied and, therefore, extra CO2 must be supplied from an external source. This source may be a nearby CO2 producer or liquid CO2 storage. It is important to minimise CO2 losses from the alkylene oxide to alkylene glycol section of the process during start-up. CO2 losses may be caused due to increased dissolution in the liquid streams at low temperature and subsequent venting of CO2 from later hydrolysis reactors and the purification stages.

Therefore, in a preferred embodiment of the present invention, the alkylene oxide to alkylene glycol section is initially pressurised with nitrogen. The carboxylation and hydrolysis reactors are heated up before CO2 is added and the recycle CO2 stream is started up just before the aqueous alkylene oxide stream is provided from the alkylene to alkylene oxide section of the process. Further, during the start-up procedure, the increased volume of CO2 venting in the later hydrolysis reactors and the dehydrator may be recovered and recycled to the CO2 recycle stream.

FIG. 1 shows possible embodiments of the start-up procedure of the present invention.

In the process for the production of an alkylene glycol from an alkene, an aqueous alkylene oxide stream (1) from the alkylene to alkylene oxide part of the process, provided via an inlet (1a), is mixed with water (2), a catalyst stream (15) and carbon dioxide (3) before being supplied to the first of the one or more carboxylation reactors (4). These carboxylation reactors have liquid recycles (5a and 5b). The stream comprising alkylene carbonate (6) is passed to a CO2 separation vessel (7). Excess carbon dioxide is recycled via a recycle stream (8). The stream comprising alkylene carbonate is then fed into the first of the one or more hydrolysis reactors (9), where it is converted to a stream comprising alkylene glycol (10). Carbon dioxide produced in a hydrolysis reactor is recycled via recycle stream (8). The stream comprising alkylene glycol (10) is then dehydrated in a dehydrator (11) to provide a dehydrated alkylene glycol stream (12) and water (17). The dehydrated alkylene glycol stream (12) is purified in one or more glycol distillation columns (13) to provide a purified alkylene glycol product stream (14) and a catalyst recycle stream (15).

During the start-up procedure for said process, little or no aqueous alkylene oxide stream (1) from the alkylene to alkylene oxide part of the process, will initially be provided via the inlet (1a). Carbon dioxide (3), water (2) and a catalyst stream (15) will be provided and a start-up stream comprising alkylene glycol will be provided at an injection point (16) which can be at any of the points (16) indicated which are at or downstream of the inlet (1a) used in step iii) of the process of the present invention.

FIG. 2 shows one preferred embodiment of the start-up procedure of the present invention. In the start-up procedure shown in FIG. 2, the injection point (16) is at the inlet (1a) and upstream of the one or more carboxylation reactors (4). During the start-up procedure, the start-up stream comprising alkylene glycol is initially supplied from an external source (19). As the procedure progresses, the start-up stream may be obtained from a glycol recycle stream (18) comprising at least a part of the purified alkylene glycol stream (14) recovered from the glycol distillation column (13). At the end of the start-up procedure, the glycol recycle stream will be stopped.

FIG. 3 shows another preferred embodiment of the present invention. In the start-up procedure shown in FIG. 3, the injection point (16) is at the inlet (1a) and into the catalyst recycle stream (15). During the start-up procedure, the start-up stream comprising alkylene glycol is initially supplied from an external source (19). As the procedure progresses, the start-up stream may be obtained from a glycol recycle stream (18) comprising at least a part of the purified alkylene glycol stream (14) recovered from the glycol distillation column (13). At the end of the start-up procedure, the glycol recycle stream, if present, will be stopped.

FIG. 4 shows a further preferred embodiment of the present invention. In the start-up procedure shown in FIG. 4, the injection point (16) at the inlet (1a) and is into the liquid recycle (5a) of the first of the one or more carboxylation reactors. As with the other preferred embodiments, during the start-up procedure, the start-up stream comprising alkylene glycol is initially supplied from an external source (19). As the procedure progresses, the start-up stream may be obtained from a glycol recycle stream (18) comprising at least a part of the purified alkylene glycol stream (14) recovered from the glycol distillation column (13). At the end of the start-up procedure, the glycol recycle stream will be stopped.

By applying the start-up procedure of the present invention, the catalyst concentration across (at least part of) the alkylene oxide to alkylene glycol section of the process can be controlled at the desired values during start-up. The further upstream the injection point is in the alkylene oxide to alkylene glycol section, the more of said section can be controlled in this manner.

This allows the entire alkylene oxide to alkylene glycol section from the point of alkylene oxide injection until alkylene glycol distillation to be in a mode of operation that is as close as possible, hydraulically and in terms of catalyst concentrations, to the situation during normal operation. By careful selection of the injection points of the mixture of alkylene glycol, water, and optionally heaver glycols, the concentration of the catalyst solution is prevented from varying widely over the various parts of the alkylene oxide to alkylene glycol reaction section. As a consequence, high and low concentrations can be maintained where they are required in the glycol section.

Further, by following the start-up procedure of the present invention, it is not necessary to bypass the catalyst separation section during the initial phases of start-up. Any problems starting this section will then occur at the beginning of the start-up and not at a later and more critical stage.

Furthermore, the simple and efficient start-up procedure of the present invention can be put in place quickly if the alkylene oxide section is shut down or is tripped and the alkylene oxide to alkylene glycol section of the process can, therefore, be maintained at stable conditions while the alkylene oxide section is re-started.

The invention claimed is:

1. A process for the production of an alkylene glycol from an alkene comprising the steps of:
   i) converting the alkene in the presence of oxygen and an epoxidation catalyst to the corresponding alkylene oxide in an epoxidation reactor;
   ii) absorbing the alkylene oxide in an aqueous absorbent and then stripping said absorbent to provide an aqueous alkylene oxide stream;
   iii) supplying the aqueous alkyene oxide stream at an inlet to a carboxylation reactor;
   iv) converting the aqueous alkylene oxide stream in the presence of one or more carboxylation-hydrolysis catalysts and carbon dioxide to a stream comprising the corresponding alkylene carbonate in one or more carboxylation reactors;
   v) converting the stream comprising the alkylene carbonate to a stream comprising the alkylene glycol in one or more hydrolysis reactors;
   vi) removing water from the stream comprising the alkylene glycol to form a dehydrated alkylene glycol stream in one or more dehydration columns;
   vii) purifying the dehydrated alkylene glycol stream in one or more glycol distillation columns to form a purified alkylene glycol product stream and a carboxylation-hydrolysis catalyst recycle stream,
   wherein the start-up procedure for said process comprises supplying water, carboxylation-hydrolysis catalyst and carbon dioxide streams to the carboxylation reactor and providing a start-up stream comprising the alkylene glycol at an injection point at or downstream of the inlet used in step iii) and recovering an alkylene glycol stream from the glycol distillation column.

2. A process according to claim 1, wherein during the start-up procedure at least part of the alkylene glycol stream recovered from the glycol distillation column is recycled to the injection point.

3. A process according to claim 1, wherein the start-up stream is provided at a point selected from the group comprising upstream of the one or more carboxylation reactors; in a liquid recycle stream recycled into any one of the one or more carboxylation reactors; between the carboxylation reactors and the one or more hydrolysis reactors; between the hydrolysis reactors if there is more than one hydrolysis reactor present; after the one or more hydrolysis reactors and before the dehydration column; into the dehydrated alkylene glycol stream before the glycol distillation column; or into the catalyst recycle stream.

4. A process according to claim 3, wherein the start-up stream is provided upstream of the one or more carboxylation reactors.

5. A process according to claim 3, wherein the start-up stream is provided into the catalyst recycle stream.

6. A process according to claim 3, wherein the start-up stream is provided into a liquid recycle stream recycled into any one of the one or more carboxylation reactors.

7. A process according to claim 6, wherein the start-up stream is provided into a liquid recycle stream recycled into the first of the one or more carboxylation reactors.

8. A process according to claim 1, wherein the alkene is ethylene.

* * * * *